(12) United States Patent
Nee

(10) Patent No.: US 6,980,112 B2
(45) Date of Patent: Dec. 27, 2005

(54) EMERGENCY CALL PATIENT LOCATING SYSTEM FOR IMPLANTED AUTOMATIC DEFIBRILLATORS

(75) Inventor: Wright Jacken Nee, Rochester, MN (US)

(73) Assignee: International Business Machines Corporation, Armonk, NY (US)

( * ) Notice: Subject to any disclaimer, the term of this patent is extended or adjusted under 35 U.S.C. 154(b) by 27 days.

(21) Appl. No.: 10/041,937

(22) Filed: Jan. 8, 2002

(65) Prior Publication Data

US 2003/0128121 A1   Jul. 10, 2003

(51) Int. Cl.$^7$ ............................................. G08B 23/00
(52) U.S. Cl. ............................ 340/573.1; 340/539.12; 600/508
(58) Field of Search .................. 340/573.1, 539.12, 340/539.16, 539.13; 607/27, 57, 30; 128/843, 128/899; 600/508, 517, 500; 455/404.1; 379/40

(56) References Cited

U.S. PATENT DOCUMENTS

| | | | |
|---|---|---|---|
| 3,927,663 A | 12/1975 | Rusell et al. ............... 128/2.06 |
| 4,432,375 A | 2/1984 | Angel et al. ................. 128/705 |
| 4,523,595 A | 6/1985 | Zibell .......................... 128/419 |
| 4,830,006 A | 5/1989 | Haluska et al. ............. 128/419 |
| 4,890,621 A | 1/1990 | Hakky ......................... 128/635 |
| 5,411,537 A | * | 5/1995 | Munshi et al. ................ 607/33 |
| 5,673,692 A | 10/1997 | Schulze et al. ............. 128/633 |
| 5,674,249 A | 10/1997 | De Coriolis et al. ............ 607/5 |
| 5,720,770 A | * | 2/1998 | Nappholz et al. ............. 607/30 |
| 5,772,585 A | 6/1998 | Lavin et al. ................. 600/300 |
| 6,045,513 A | 4/2000 | Stone et al. ................. 600/508 |
| 6,112,116 A | 8/2000 | Fischell et al. ............. 600/517 |
| 6,263,245 B1 | * | 7/2001 | Snell ............................ 607/60 |
| 6,272,379 B1 | 8/2001 | Fischell et al. ................ 607/5 |
| 6,275,734 B1 | 8/2001 | McClure et al. .............. 607/27 |
| 6,280,409 B1 | 8/2001 | Stone et al. ................... 604/67 |
| 6,292,698 B1 | * | 9/2001 | Duffin et al. ................. 607/32 |
| 6,443,890 B1 | 9/2002 | Schulze et al. ............. 600/300 |
| 6,468,219 B1 | * | 10/2002 | Njemanze ................... 600/454 |
| 6,478,736 B1 | 11/2002 | Mault .......................... 600/300 |
| 6,553,262 B1 | * | 4/2003 | Lang et al. ................... 607/32 |
| 6,553,263 B1 | * | 4/2003 | Meadows et al. ............. 607/61 |
| 6,564,104 B2 | * | 5/2003 | Nelson et al. ................ 607/60 |
| 6,579,231 B1 | 6/2003 | Phipps ....................... 600/300 |
| 2002/0109600 A1 | 8/2002 | Mault ...................... 340/573.1 |

OTHER PUBLICATIONS http://www.skyaid.org/LifeWatch/life_watch.htm, accessed on Sep. 19, 2001, LifeWatch: The wristwatch that can save a life, updated Sep. 6, 2001, pp. 1-5.

Implant tells your doctor how you're doing, by Lauran Neergaard, Associated Press.

http://seattlep-i.nwsource.com/national/42402_health12.shtml, accessed on Oct. 23, 2001, FDA approves new pacemaker that can monitor patients, Oct. 12, 2001, pp. 1-3.

(Continued)

*Primary Examiner*—Phung T. Nguyen
(74) *Attorney, Agent, or Firm*—Patterson & Sheridan LLP

(57) ABSTRACT

Methods and systems for placing a distress call in response to the operation of an implanted device. The implanted device may be any of a plurality of medical devices capable of monitoring and/or regulating an organ. When threshold conditions are reached, a distress signal transmitted by the implanted device activates an external communications system. The external communications system then places a distress call, which may be responded to by the appropriate medical personnel.

22 Claims, 4 Drawing Sheets

OTHER PUBLICATIONS http://www.washingtonpost.com/wp-srv/aponline/20011012/aponine035439_000.htm, acessed on Oct. 23, 2001, FDA Approves High Tech Pacemaker, dated Oct. 12, 2001, pp. 1-3.

John Lortz and Susan Leavitt, "What is Bluetooth? We Explain the Newest Short-Range Connectivity Technology," 2002, Sandhill Publishing, Smart Computing Learning Series Wireless Computing, pp 72-74.

* cited by examiner

EMERGENCY CALL PATIENT LOCATING SYSTEM FOR IMPLANTED AUTOMATIC DEFIBRILLATORS

BACKGROUND OF THE INVENTION

1. Field of the Invention

The present invention generally relates to medical devices. More particularly, the invention relates to methods and systems for transmitting a distress call in response to a signal from an implanted unit.

2. Description of the Related Art

Implantable medical devices, such as implantable cardiac devices, are devices which are implanted in the body of a patient and are capable of monitoring the function of a patient's organ, such as their heart or brain, and are further configured in some instances to be able to deliver therapeutic electrical stimulation to the patient's organ.

Implantable cardiac devices, such as pacemakers and implantable cardioverter defibrillators (ICDs), are very commonly used implantable mechanical devices and are used to treat various heart conditions. These types of implantable cardiac devices typically have one or more leads that are positioned adjacent the walls of the heart and a control unit which receives signals indicative of the functioning of the heart. The control unit induces the delivery of therapeutic electrical stimulation to the walls of the heart via the leads in response to sensed heart conditions. Generally, the control unit incorporates a processor that is capable of recognizing and discerning particular heart irregularities based upon the signals that the processor receives. The implanted leads act as a sensor that delivers an intracardial electrogram (IEGM) to the processor, which provides the processor with a signal that is indicative of the heart function. Hence, the processors of these types of implantable cardiac devices continuously receive an IEGM signal that allows the processor to determine whether therapeutic stimulation of the heart is needed to regulate the heart function.

Despite the general effectiveness of implanted devices, patients using these devices often require additional medical attention. Such a need may arise, for example, in the event that the implanted device fails or malfunctions. Often, the patient may be physically unable to call for help due to pain, confusion, loss of consciousness, etc.

Recently, systems capable of real-time monitoring have been made available. One such system is the Home Monitoring System available from Biotronik, Inc. Real-time monitoring systems download information from a pacemaker and, ultimately, transmit the downloaded information to a physician. However, the operation of such real-time monitoring systems is not dependent upon, or triggered by, the condition of the patient being monitored. Rather, the downloading and transmitting of information occurs at a preset interval. A determination that the patient requires medical attention can only be made by the doctor after receiving and reviewing the downloaded information. Because the downloaded information does not explicitly notify the physician of a possible emergency condition, the physician is not motivated to take immediate emergency action. As a result, critical time may pass between the time the information is made available for review and the time that the information is actually reviewed. Further, existing real-time monitoring systems are limited to use with pacemakers and are not used in conjunction with other implanted devices, such as implanted defibrillators.

Therefore, there is a need for a method and system of enhancing the utility of implanted devices where medical attention may be required.

SUMMARY OF THE INVENTION

The present invention generally provides methods and systems for placing a distress call in response to the operation of an implanted device.

One embodiment provides a method for selectively placing a distress call in response to activity of an implanted medical device. The method comprises receiving a wireless signal from the implanted medical device and transmitting the distress call to a remote location in response to receiving the wireless signal.

Another embodiment provides a system for selectively placing a distress call. The system comprises a wireless external receiver configured to receive a wireless signal from an implanted medical device; and an external communications device connected to the wireless external receiver. The external communications device is configured to transmit a distress call to a remote location in response to receiving input from the wireless external receiver.

Still another embodiment provides an implantable medical device comprising an organ monitoring device configured to monitor activity of an organ; and a wireless transmitter in communication with the organ monitoring device. The wireless transmitter is configured to selectively transmit a wireless distress signal in response to predetermined activity of the organ.

BRIEF DESCRIPTION OF THE DRAWINGS

So that the manner in which the above recited features of the present invention are attained and can be understood in detail, a more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

DETAILED DESCRIPTION OF THE PREFERRED EMBODIMENTS

The present invention generally provides methods and systems for placing a distress call in response to the operation of an implanted device. The implanted device may be any of a plurality of medical devices capable of monitoring and/or regulating an organ. When threshold conditions are reached, a distress signal transmitted by the implanted device activates an external communications system. The external communications system then places a distress call, which may be responded to by the appropriate medical personnel.

Figure 1:
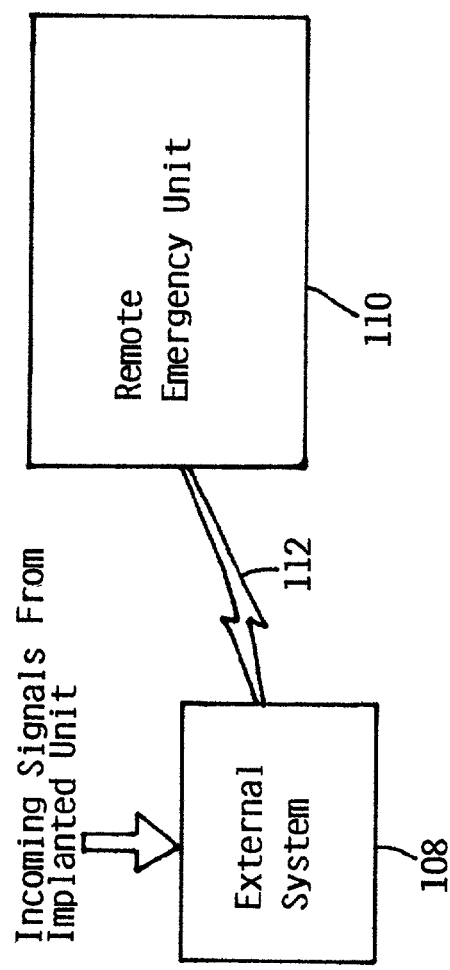
FIG. 1 is a diagram of an implanted system configured to cause an external system to place a distress call.
Figure 1:
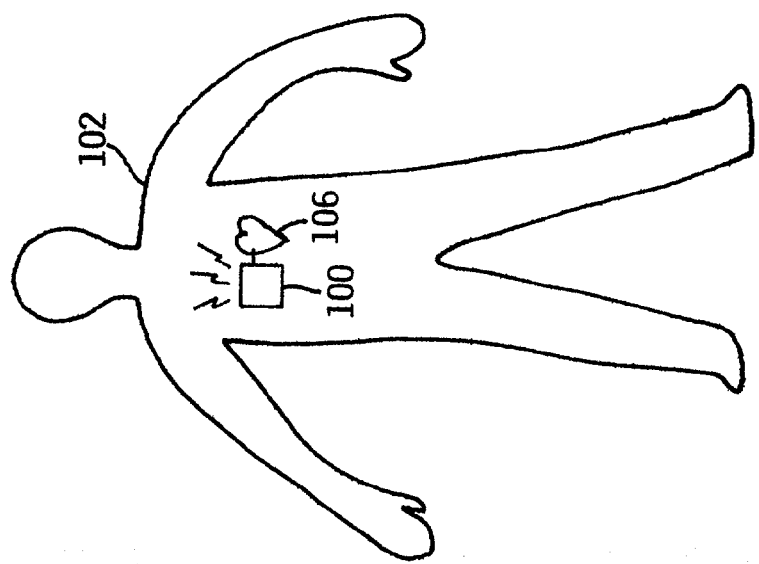

Some or all aspects of the invention may be implemented as a program product for use with a computer system such as, for example, an implanted system 100 and/or external system 108, both shown in FIG. 1. The program(s) of the program product defines functions of the embodiments (including the methods described below) and can be contained on a variety of signal-bearing media. Illustrative signal-bearing media include, but are not limited to: (i) information permanently stored on non-writable storage media (e.g., read-only memory devices within a computer such as CD-ROM disks readable by a CD-ROM drive); (ii) alterable information stored on writable storage media (e.g., floppy disks within a diskette drive or hard-disk drive); or (iii) information conveyed to a computer by a communications medium, such as through a computer or telephone network, including wireless communications. The latter embodiment specifically includes information downloaded from the Internet and other networks. Such signal-bearing media, when carrying computer-readable instructions that direct the functions of the present invention, represent embodiments of the present invention.

In addition, various programs/instructions described hereinafter may be identified based upon the application for which they are implemented in a specific embodiment of the invention. However, it should be appreciated that any particular program/instructions nomenclature that follows is used merely for convenience, and thus the invention should not be limited to use solely in any specific application identified an/or implied by such nomenclature.

While functions of the invention may be implemented in software, the same functions may also be implemented in hardware. For example, hardwired embedded controllers and Application Specific Integrated Circuits (ASIC) may be used.

Reference will now be made the drawings wherein like numerals refer to like parts throughout. Referring to FIG. 1, a human subject (also referred to herein as the "patient") 102 is shown with an implantable medical device system 100 (also referred to herein as the "the system 100" and "the implantable system 100"). The system 100 is adapted to be implanted in the human subject 102 in a well-known manner. The system 100 can be comprised of any implantable device including a pacemaker or an implantable cardioverter defibrillator (ICD) or any implantable device incorporating the functionality of both a pacemaker and an ICD. In the illustrated embodiment, the system 100 comprises an implantable cardiac device and, as such, is shown in connection with a heart 106. While embodiments are discussed in connection with an implantable cardiac device, it will be appreciated from the following discussion that any implantable device that measures the intrinsic activity of one of the patient's organs are contemplated as embodiments of the invention. Further, the particular implanted system may or may not deliver signals to the organ being monitored for purposes of regulating a desired operation of the organ. It is further contemplated that the implanted system 100 not be limited to monitoring/regulating an organ. Accordingly, other devices within the scope of the invention may include neural devices for providing therapeutic stimulation to portions of the brain and devices that monitor organ activity such as ECG monitors, brain-wave monitors, glucose monitors and other types of monitors known in the art.

In addition to monitoring and regulating the operation of the heart 106, the system 100 is configured to selectively transmit signals to an external system 108. In one embodiment, the transmitted signals are distress signals indicating cardiac failure or some other emergency condition. The signals may be transmitted, for example, at each instance the system 100 detects abnormal operation of the heart 106. Alternatively, the distress signals may be transmitted to the external system 108 only after the system 100 has attempted to stabilize the heart 106 (such as by providing electrical signals to the heart 106 via a pulse generator) a threshold number of times within a predetermined time period. Further, the distress signals may be transmitted to the external system even in cases where the heart 106 is operating normally. For example, the power level of the system may be dangerously low. The low battery power may trigger the distress signal. In other cases, it may be desirable to anticipate an imminent low battery power situation and proactively trigger the distress signal to notify the patient 102 and/or an emergency unit 110 (described below).

In one embodiment, both the implanted system 100 and the external system 108 are configured with short range communications devices capable of communicating with one another. As such, successful communications between the implanted system 100 and external system 108 depend on their relative close proximity. As defined herein, "close proximity" means any distance at which the implanted system 100 and external system 108 are capable of communicating with one another. Persons skilled in the art will recognize that a particular effective distance is dependent upon the technical specifications (e.g., transmission power, signal strength, susceptibility to interference, etc.) of the implanted system 100 and the external system 108. Further, the effective distance between the implanted system 100 and external system 108 may be increased by the provision of external relay devices capable of augmenting or boosting the transmission signal from the implanted device 100.

In general, the external system 108 is any device configured to transmit a distress call to a remote emergency unit 110, in response to the distress signal(s) received from the system 100. In one embodiment, the external system 108 is a mobile telephone (e.g., cell phone) adapted to process the distress signal(s) received from the system 100. A distress call may then be placed to the remote emergency unit 110 via a network 112. The network 112 may be a telephone network, a broadband Internet network or any other type of network, according to the particular technology implemented in the external system 108.

The remote emergency unit 110 may be a hospital, a doctor, an emergency unit dispatcher and the like. Alternatively, the remote emergency unit 110 may be an intermediary base station at which the distress call is received and then forwarded to the appropriate medical authority. It is contemplated that, in one embodiment, information provided to the remote emergency unit 110 includes at least the patient's location. In another embodiment, the patient's location may be determined by other techniques, such as by cell triangulation, or be provided by the patient himself. The information may also include the patient's name and the particular condition that caused the distress call to be made (e.g., heart failure). In one embodiment, the information may be used to initiate an automated data retrieval process, whereby the patient's medical records are retrieved (from a database) and made available for viewing by a human operator at the remote emergency unit 110. Of course, such a data retrieval process may be manually implemented once the information is received by the human operator from the external system 108.

Figure 2:
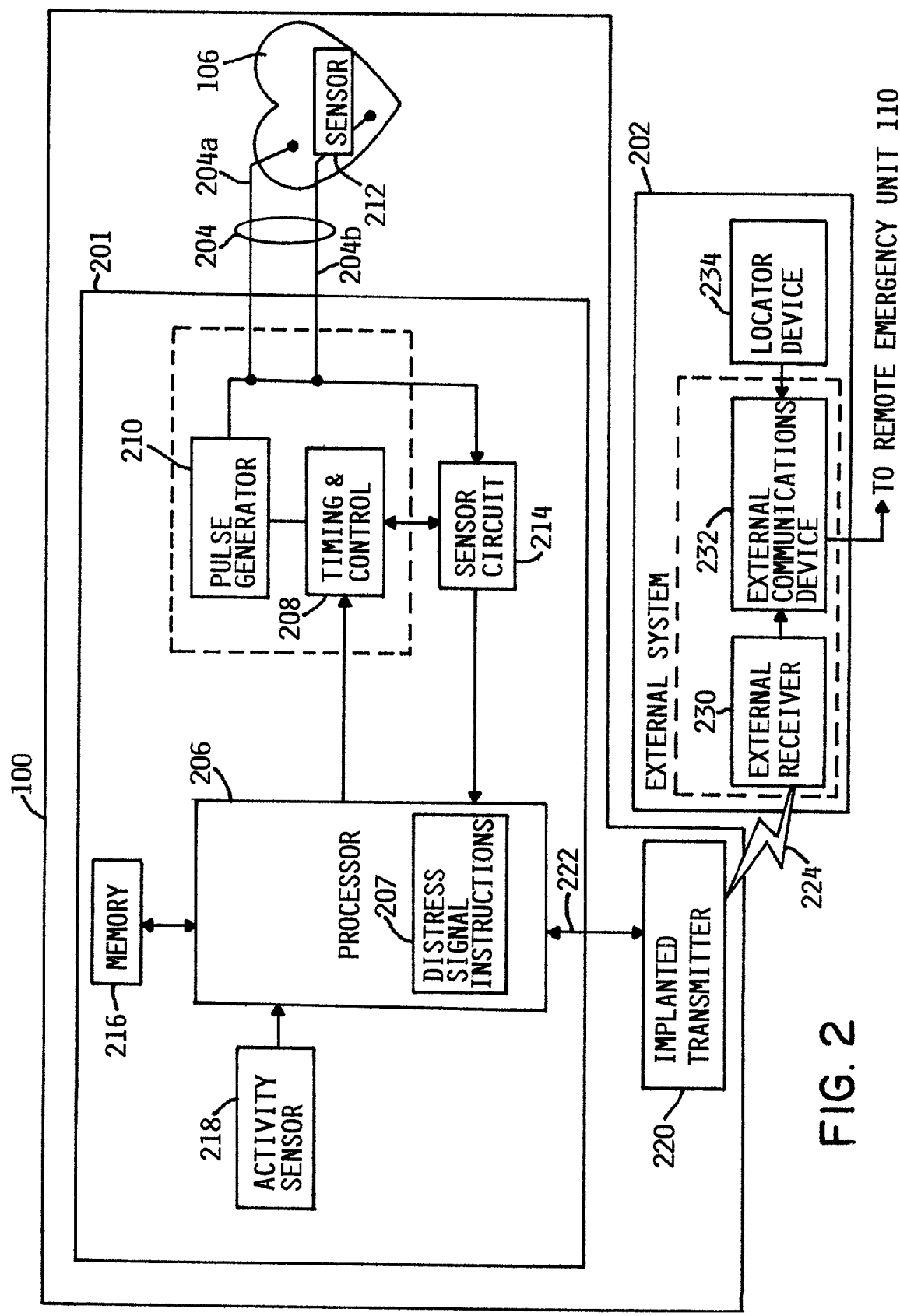
FIG. 2 is a block diagram of one embodiment of an implanted unit in communication with an external system.

Referring to FIG. 2, a functional block diagram of one embodiment of the implantable medical device system 100 and an external system 202 is shown. The external system 202 is representative of one embodiment of the external system 108 shown in FIG. 1. The system 100 generally comprises a control unit 201 and a plurality of leads 204a and 204b (collectively referred to as leads 204) that are adapted to be positioned within, or proximate to, the chambers of a patient's heart 106. The control unit 201 includes a processor 206 that provides output signals to a timing and control circuit 208. Upon receipt of the output signals from the processor 206, the timing and control circuit 208 induces a pulse generator 210 to produce therapeutic electrical stimulation, e.g., pacing pulses or cardioversion or defibrillation waveforms, that is transported via the leads 204 to stimulate the heart 106. The exact function of the processor 206 in inducing the delivery of the therapeutic electrical stimulation to the heart is performed in any of a number of well-known manners. For example, in one embodiment, the processor 206 induces pacing pulses to be delivered to the apex of the ventricle of the heart 106. In another embodiment, the processor 206, upon sensing the occurrence of a particular tachycardia, induces defibrillation or cardioversion stimuli to be delivered to the heart.

Further, the processor 206 receives input signals from a sensor 212 via a sensor circuit 214. In one embodiment, the sensor 212 is comprised of an implanted lead 204 that is positioned within one of the chambers of the heart 106 so as to provide an intracardiac electrogram (IEGM) signal to the processor 206. The IEGM signal is provided to the sensor circuit 214 and may be further processed by the sensor circuit 214 so that the processor 206 receives a filtered IEGM signal that the processor 206 can use in determining whether to deliver therapeutic electrical stimulation to the heart via the timing and control circuit 208 and the pulse generator circuit 210.

The processor 206 may also receive signals from an activity sensor 218 which allows the processor 206 to modify the delivery of therapeutic electrical stimulation to the heart 106. The system 100 may provide therapy to the heart 106 according to methods known in the art of implantable cardiac devices.

In the illustrated embodiment, the processor 206 also has an associated memory 216 wherein information, such as IEGM signals, can be stored for subsequent transmission to the external system 202. Additionally or alternatively, the memory 216 may contain programming executable by the processor 206. In one embodiment, the memory 216 contains operational data for the implanted system 100. Operation data may include, for example, the number of electrical charges delivered to the heart 106, the intensity of the charges, the range of frequencies of charges, etc. The memory 216 may also contain manufacturing information such as a serial number and model number, place of manufacture, date of manufacture, etc.

In operation, one or more of the leads 204 of the sensor 212 are implanted within, or proximate to, the chambers of the heart so as to be able to provide an intracardiac electrogram (IEGM) signal to the processor 206 in a well known manner. This signal is indicative of the functioning of the heart and can be used by the processor 206 to ascertain whether certain criteria have been met that necessitate the delivery of therapeutic electrical stimulation to the heart to regulate heart function. For example, the processor 206 may review the IEGM signal and, upon detecting a ventricular tachycardia or fibrillation, may induce a cardioversion or defibrillation shock to be delivered by the leads 204 in a manner that is known in the art. Similarly, the processor 206 may also use the IEGM signal as a basis for delivering a pacing pulse to the apex of the ventricle of the heart 106 so as to induce a paced heart activity in a demand pacing regime.

Further, the processor 206 is configured with distress signal instructions 207. In general, the distress signal instructions 207 are executed in response to signals from the sensor circuit 214. The distress signal instructions 207 are executed by the processor 206 in order to determine whether to activate an implanted transmitter 220.

The implanted transmitter 220 maybe any short-range communications device capable of communicating with the external system 202. In one embodiment, the implanted transmitter 220 is an RF telemetry device. The processor 206 and the implanted transmitter 220 are connected via a communication path 222 which may be a wireless connection or a hardwired connection (e.g., a hardwired bus, an optical connection, etc.). While shown separately from the control unit 201, the implanted transmitter 220 may be integrated with the control unit 201.

In general, the external system 202 is configured for receiving, transmitting and determining patient location. As such, the external system 202 comprises an external receiver 230, an external communications device 232 and a locator device 234. The external receiver 230 is any communication device capable of wireless communication (via connection 224) with the implanted transmitter 220. For example, where the implanted transmitter 220 is an RF telemetry device, the external receiver 230 is also an RF telemetry device. The external receiver 230 is connected to the external communications device 232 and provides information received from the implanted transmitter 220 thereto. The external communications device 232, in turn, is configured to place a distress call to the remote emergency unit 110 (shown in FIG. 1). The distress call also includes a location of the external system 202, which is provided to the external communications device 232 by the locator device 234. Illustrative locator devices include a global positioning system (GPS), a SnapTrack GPS system, etc. As noted above, other techniques for location determination are contemplated, such as cell triangulation.

In one embodiment, the system 100 transmits information to the external system 202 only in the event of emergency condition (e.g., as determined by the distress signal instructions 207). Alternatively, the system 100 may continuously transmit information (both emergency information and non-emergency information) to the external system 202. Illustrative non-emergency information includes status information about the organ being monitored by the system 100. The external system 202 may then take steps to determine whether the information indicates an emergency condition.

The external system 202 is preferably a self-contained unit configured to communicate with the implanted transmitter 220 via the wireless connection 224 and with the remote emergency unit 110 via the network connection 112. In one embodiment, the external system 202 is a portable unit that the patient 102 may carry on their person (e.g., by means of a shoulder harness, a waist support, a wrist band, a purse, etc.). As such, it is contemplated that the wireless connection 224 is unique and that a particular system 100 is configured for communicating with a particular external system 202. However, it is also contemplated that the external system 202 is configured to communicate with a plurality of implanted systems 100, each of which is implanted in a different patient. In such embodiment, the implanted transmitters may be distinguished from one another by the external system 202 by transmitting a unique digital identifier (ID), operating at different frequencies, etc.

Such an implementation is particularly advantageous where a network of external systems 202 is installed, such that each external system 202 is an access point to a communications network (e.g., a telephone communication network, a wide area network (WAN), etc.). So long as the patient 102 is within a range sufficient to maintain the wireless connection 224, the appropriate information may be exchanged between the implanted system 100 and the external system 202. In this manner, the patient 102 is freed from the burden of having to carry, or otherwise be concerned with the proximity of, a particular external system 202.

Figure 3:
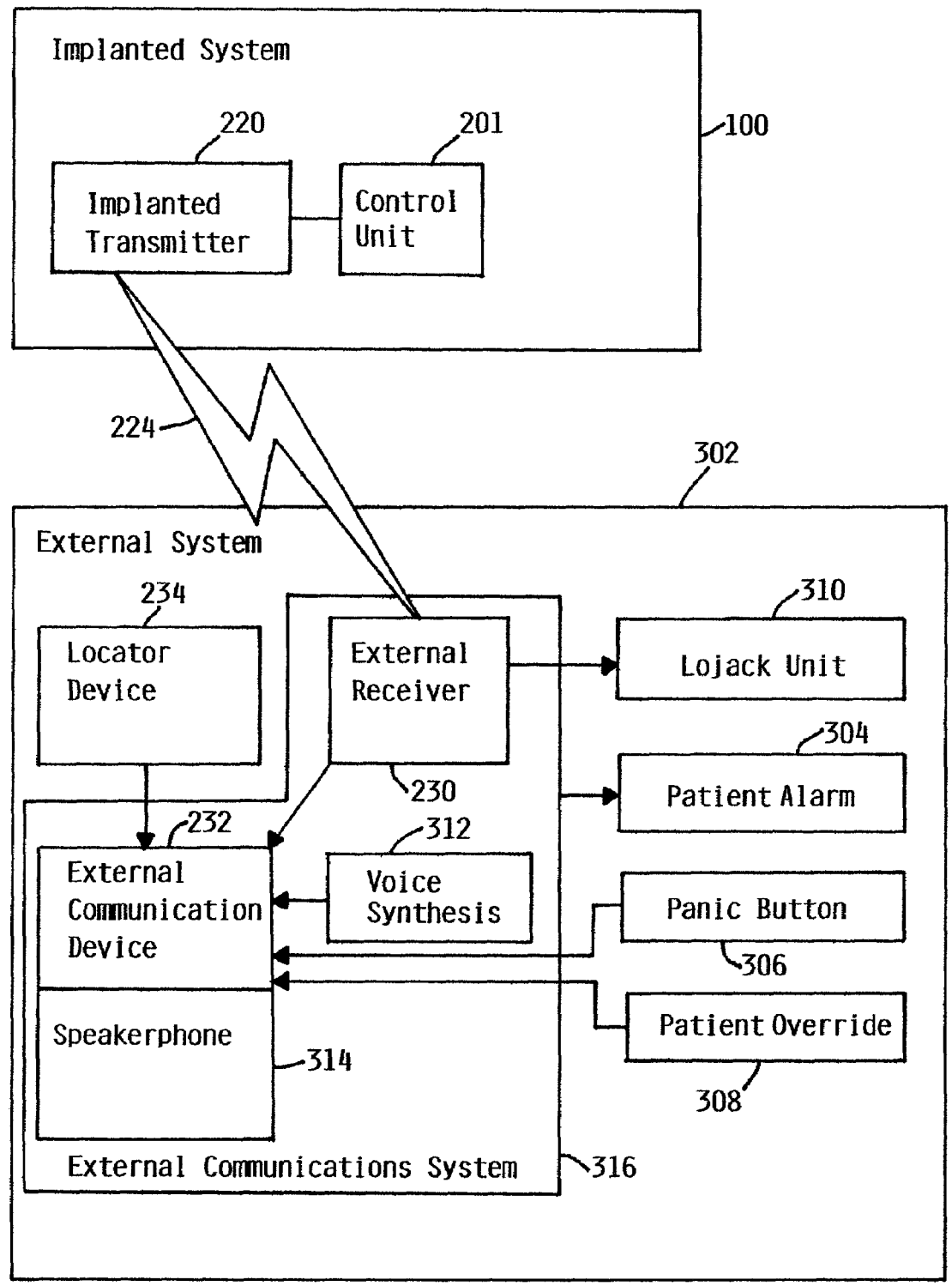
FIG. 3 is a block diagram of another embodiment of a external system.

Referring now to FIG. 3, another embodiment of an external system 302 is shown. Some of the components of the external system 302 are the same as those of the external system 202 described above with reference to FIG. 2. Accordingly, like numerals identified like components which have already been described above. The additional or alternative components shown in FIG. 3 include a patient alarm 304, a panic button 306, a patient override button 308, a LoJack unit 310, a voice synthesizer 312 and a speakerphone 314.

The patient alarm 304 is an output device configured to indicate that a condition being monitored for has been detected. Illustratively, the alarm may be an audible alarm, a vibrating alarm, a visual alarm (e.g., text or graphical display) or a combination thereof. In the case of a visual alarm, it is contemplated that information may be displayed on a display screen of the external communications device 232, e.g., on a wireless phone display. The patient alarm 304 is particularly useful for non-emergency conditions in which a distress call is not warranted, but the patient 102 needs to be alerted about a condition (e.g., low battery power of the implanted system 100).

The panic button 306 allows the patient 102 to manually activate the external system 302. In one embodiment, when the panic button 306 is pressed, a signal is sent from the external system 302 to the implanted system 100 requesting vital data. Once received by the external system 302, the vital data may be provided to the remote emergency unit 110 (shown in FIG. 1). Alternatively or additionally, pressing the panic button 306 may simply initiate a distress call to the remote emergency unit 110 without first requesting information from the implanted system 100. In another embodiment, the functions of the panic button 306 may be implemented by producing a magnetic field proximate the implanted system 100. The magnetic field may be generated by a magnet held by the patient 102. This technique is well known in the art and is used, for example, by the Biotronik Home Monitoring System.

The patient override button 308 allows the patient 102 to intercept and terminate distress calls from the external system 202 to the remote emergency unit 110. Alternatively or additionally, the patient override button 308 may be configured to allow the patient 102 to deactivate selected portions of the implanted system 100 and/or the external system 302.

The LoJack unit 310 is a widely known stolen vehicle recovery system. The LoJack unit 310 is equipped with a locator device that transmits a signal to a remote receiving device. The signal, once detected, can be tracked to its source. The LoJack unit 310 may be used to advantage in the present invention as an alternative to, or in conjunction with, the locator device 234.

Illustratively, the voice synthesizer 312 and the speakerphone 314 are components of an external communications system 316. The synthesizer 312 is configured to generate a voice message that can be transmitted to the remote emergency unit 110 via the external communications device 232. In this manner, the voice message may be output to personnel at the remote emergency unit 110 without the need for specialized decoding equipment.

Figure 4:
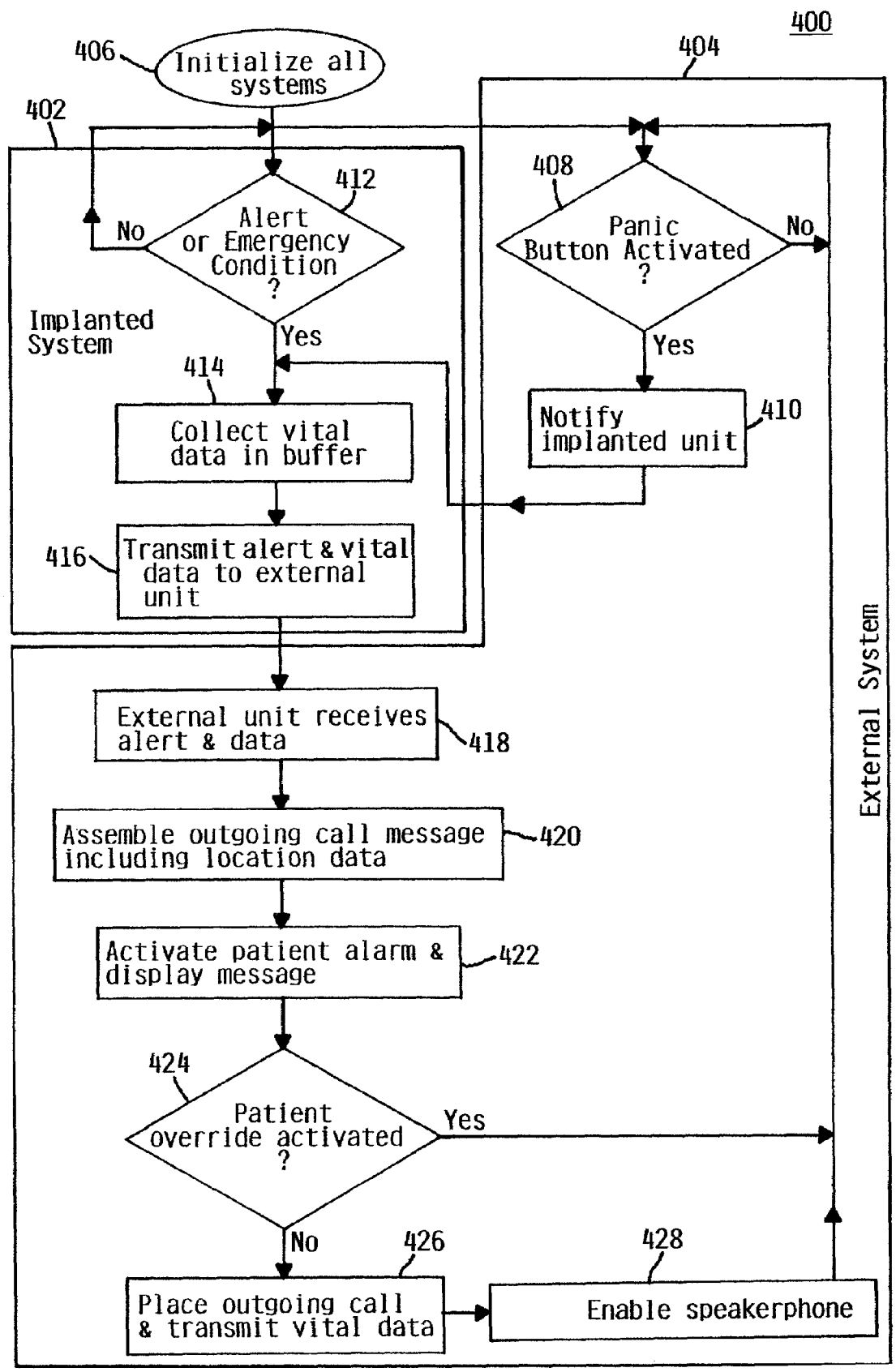
FIG. 4 is a flow diagram illustrating the operation of the implanted system and the external system.

Referring now to FIG. 4, a method 400 is shown illustrating the operation of the implanted system 100 and the external system 108 (202, 302). The method 400 generally includes a first routine 402 illustrating one embodiment of the operation of the implanted system 100 and a second routine 404 illustrating one embodiment of the operation of the external system 108.

The method 400 is entered at step 406 where all systems are initialized. Processing for the implanted system 100 then proceeds to step 412 of the first routine 402 while processing for the external system 108 proceeds to step 408 of the second routine 404. At step 408, the external system 108 queries whether the panic button 306 has been activated. If so, a request for vital data is transmitted to the implanted system 100 at step 410. Processing then proceeds to step 414 where the implanted system 100 collects vital data in a buffer (e.g., memory 216). If not, processing returns to repeat step 408.

Returning to the implanted system routine 402, at step 412 the implanted system 100 queries whether an alert or emergency condition has been detected. If not, processing returns to repeat step 412. If, however, an alert or emergency condition is detected, a distress signal and vital data is transmitted from the implanted system 100 to the external system 108 at step 416.

The information transmitted at step 416 is received by the external system 108 at step 418. At step 420, the external system 108 assembles an outgoing distress call, including location information provided by the locator device 234. The patient alarm 304 is then activated at step 422. The external system 108 then queries, at step 424, whether the patient override button 308 has been pressed. If so, the outgoing distress call is terminated and processing returns to step 408. If the patient override button 308 has not been pressed, the distress call and vital data are transmitted at step 426. Optionally, the speakerphone 314 is enabled at step 428 to allow for voice communication between the patient and the remote emergency unit 110. Once the call is disconnected, the speakerphone may be disabled and the second routine 404 then returns to step 408. The foregoing processing may continue so long as the implanted system 100 and the external system 108 are functioning.

While the foregoing is directed to embodiments of the present invention, other and further embodiments of the invention may be devised without departing from the basic scope thereof, and the scope thereof is determined by the claims that follow.

What is claimed is:

1. A method for selectively placing a distress call in response to activity of an implanted medical device worn by a human subject, comprising:
   receiving a wireless signal from the implanted medical device; and
   in response receiving the wireless signal:
      generating, by an external voice synthesizer, a voice synthesized message providing information about a nature of the human subject's condition even in the event the human subject wearing the implanted medical device is incapable of verbal communication; and
      transmitting, by an external communications device, the distress call in the form of the voice synthesized message to a remote location;

wherein the distress call includes at least one of a serial number and a model number of the implanted medical device.

2. The method of claim 1, wherein the wireless signal is indicative of a medical emergency experienced by the human subject wearing the implanted medical device.

3. The method of claim 1, prior to transmitting, determining that the wireless signal is indicative of a medical emergency being experienced by the human subject wearing the implanted medical device.

4. The method of claim 1, wherein the wireless signal and distress call contain vital data pertaining to an organ being monitored by the implanted medical device.

5. The method of claim 1, wherein the distress call contains location information indicating a location of a device initiating the distress call.

6. The method of claim 1, wherein the implanted medical device comprises one of a pacemaker, an implantable cardioverter defibrillator and a combination thereof.

7. The method of claim 1, wherein the implanted medical device comprises a transmitter configured to transmit the wireless signal and a heart regulating device.

8. A system for selectively placing and handling a distress call, comprising:
   an implanted medical device worn by a human subject and comprising a wireless transmitter for issuing a wireless signal;
   a wireless external receiver configured to receive the wireless signal from the implanted medical device;
   a voice synthesizer configured to generate a voice synthesized message in response to the wireless signal, the voice synthesized message providing information about a nature of the human subject's condition; and
   an external communications device communicative with the wireless external receiver and configured to transmit a distress call in the form of the voice synthesized message to a remote location in response to receiving input from the wireless external receiver even in the event the human subject wearing the implanted medical device is incapable of verbal communication;
   wherein the distress call comprises at least one of the serial number and the model number of the implanted medical device.

9. The system of claim 8, wherein the distress call contains location information indicating a location of the external communications device.

10. The system of claim 8, further comprising a locator device configured to provide location information to the external communications device, wherein the location information is included in the distress call.

11. The system of claim 8, wherein the wireless signal and distress call contain vital data pertaining to an organ being monitored by the implanted medical device.

12. The system of claim 8, wherein the implanted medical device comprises one of a pacemaker, an implantable cardioverter defibrillator and a combination thereof.

13. The system of claim 8, wherein the implanted medical device comprises a transmitter configured to transmit the wireless signal and a heart regulating device.

14. The system of claim 8, wherein the external communications device is configured to determine, prior to transmitting the distress call, that the wireless signal is indicative of a medical emergency being experienced by the human subject wearing the implanted medical device.

15. The method of claim 1, wherein the external communications device is a cell phone.

16. The method of claim 1, further comprising receiving, by the external device, a wireless power status signal from the implanted medical device indicating a low battery power of the implanted medical device.

17. The system of claim 8, wherein the external communications device is a cell phone.

18. The system of claim 8, wherein the implanted medical device is configured to transmit a wireless power status signal to the external communications device indicating a low battery power of the implanted medical device.

19. The system of claim 8, wherein the implanted medical device is configured to transmit a wireless power status signal to the external communications device indicating a low battery power of the implanted medical device.

20. A method for selectively placing and handling a distress call in response to activity of an implanted medical device worn by a human subject, comprising:
   receiving, by an external communications device, a wireless signal from the implanted medical device; and
   in response to receiving the wireless signal:
      generating, by an external voice synthesizer, a voice synthesized message providing information about a nature of the human subject's condition even in the event the human subject is incapable of verbal communication;
      transmitting the distress call, with the voice synthesized message, to a remote location in response to receiving the wireless signal;
      receiving the distress call at the remote location;
      in response to receiving the distress call at the remote location, automatically accessing a patient record from a database; and
      displaying the patient record to an operator;
   wherein the external communications device is a cell phone, and further comprising:
   inputting the voice synthesized message into the cell phone from which the voice synthesized message is transmitted with the distress call.

21. The method of claim 20, wherein the wireless signal and distress call contain vital data pertaining to an organ being monitored by the implanted medical device.

22. The method of claim 20, further comprising receiving, by the external device, a wireless status signal from the implanted medical device indicating a low battery power of the implanted medical device.

* * * * *